United States Patent [19]
Lal et al.

[11] Patent Number: 6,080,886
[45] Date of Patent: Jun. 27, 2000

[54] FLUORINATION WITH AMINOSULFUR TRIFLUORIDES

[75] Inventors: Gauri Sankar Lal, Whitehall; Guido Peter Pez, Allentown, both of Pa.

[73] Assignee: Air Products and Chemicals, Inc., Allentown, Pa.

[21] Appl. No.: 08/939,940

[22] Filed: Sep. 29, 1997

[51] Int. Cl.$^7$ .......................... C07C 17/013; C07C 29/62
[52] U.S. Cl. .......................... 560/227; 544/158; 546/248; 548/562; 548/565; 548/570; 564/102; 568/437; 568/821; 570/127; 570/144; 570/125
[58] Field of Search .......................... 564/102; 544/158; 546/248; 548/562, 565, 570; 570/142, 127, 144, 175; 560/227; 568/437, 821

[56] References Cited

U.S. PATENT DOCUMENTS

| | | | |
|---|---|---|---|
| 3,499,030 | 3/1970 | Kuhle et al. | 260/551 |
| 3,914,265 | 10/1975 | Middleton | 260/397 |
| 3,976,691 | 8/1976 | Middleton | 260/544 |

FOREIGN PATENT DOCUMENTS 433136  12/1974  Russian Federation .

OTHER PUBLICATIONS

W. J. Middleton, New Fluorinating Reagents, Dialkylaminosulfur Fluorides, *J. Org. Chem.*, vol. 40, No. 5, (1975), pp. 574–578.

Messina, et al., Aminosulfur Trifluorides: Relative Thermal Stability, *Journal of Fluorine Chemistry,* 43, (1989), pp. 137–143.

M. Hudlicky, Fluorination with Diethylaminosulfur Trifluoride and Related Aminofluorosulfuranes, Organic Reaction, vol. 35, (1988), pp. 513–553.

G. L. Hann, et al. Synthesis and Enantioselective Fluorodehydroxylation Reactions of (S)–2–(Methoxymethyl(pyrrolidin–1–ylsulphur Trifluoride, the First Homochiral Aminofluorosulphurane, J. Chem. Sol., Chem. Commun. (1989) pp. 1650–1651.

J. Cochran, Laboratory, Explosions, Chemical and Engineering News, (1979), vol. 57, No. 12, pp. 4 & 74.

W. T. Middleton, Explosive Hazards with DAST, Chemical and Engineering News, (1979), vol. 57, No. 21, p. 43.

W. J. Middleton, et al., a,a–Difluoroarylacetic Acids: Preparation from (Diethylamino)sulfur Trifluoride and x–Oxarylacetates, J. Org. Chem. (1980) 45, 2883–2887.

*Primary Examiner*—Peter O'Sullivan
*Attorney, Agent, or Firm*—Geoffrey L. Chase

[57] ABSTRACT

A fluorination method of oxygen and halogen sites with diaryl-, dialkoxyalkyl-, alkylalkoxyalkyl-, arylalkoxyalkyl- and cyclic aminosulfur trifluorides fluorinating reagents is disclosed.

20 Claims, No Drawings

FLUORINATION WITH AMINOSULFUR TRIFLUORIDES

CROSS-REFERENCE TO RELATED APPLICATIONS

Not applicable.

STATEMENT REGARDING FEDERALLY SPONSORED RESEARCH OR DEVELOPMENT

Not applicable.

BACKGROUND OF THE INVENTION

The development of safe, efficient, and simple methods for selective incorporation of fluorine into organic compounds has become a very important area of technology. This is due to the fact that fluorine strategically positioned at sites of synthetic drugs and agrochemical products significantly modifies and enhances their biological activities. The conversion of the C—O to the C—F bond, which is referred to herein a deoxofluorination, represents a viable method to produce selectively fluorinated organic compounds, but the low yields and hazards associated with the current deoxofluorination reagents and processes severely limit the application of this technique.

The introduction of fluorine into medicinal and agrochemical products can profoundly alter their biological properties. Fluorine mimics hydrogen with respect to steric requirements and contributes to an alteration of the electronic properties of the molecule. Increased lipophilicity and oxidative and thermal stabilities have been observed in such fluorine-containing compounds.

In view of the importance of organofluorine compounds, efforts aimed at the development of simple, safe, and efficient methods for their synthesis have escalated in recent years. The conversion of the carbon-oxygen to the carbon-fluorine bond by nucleophilic fluorinating sources (deoxofluorination) represents one such technique which has been widely used for the selective introduction of fluorine into organic compounds. A list of the deoxofluorination methods practiced to date includes: nucleophilic substitution via the fluoride anion; phenylsulfur trifluoride; fluoroalkylamines; sulfur tetrafluoride; $SeF_4$; $WF_6$; difluorophosphoranes and the dialkylaminosulfur trifluorides (DAST). The most common reagent of this class is diethylaminosulfur trifluoride, Et-DAST or simply DAST.

The DAST compounds have proven to be useful reagents for effecting deoxofluorinations. These reagents are conventionally prepared by reaction of N-silyl derivatives of 2° amines with $SF_4$. In contrast to $SF_4$, they are liquids which can be used at atmospheric pressure and at near ambient to relatively low temperature (room temperature or below) for most applications. Deoxofluorination of alcohols and ketones are particularly facile and reactions can be carried out in a variety of organic solvents (e.g., $CHCl_3$, $CFCl_3$, glyme, diglyme, $CH_2Cl_2$, hydrocarbons, etc.). Most fluorinations of alcohols are done at −78° C. to room temperature. Various functional groups are tolerated including CN, $CONR_2$, COOR (where R is an alkyl group), and successful fluorinations have been accomplished with primary, secondary and tertiary (1°, 2°, 3°) allylic and benzylic alcohols. The carbonyl to gem-difluoride transformation is usually carried out at room temperature or higher. Numerous structurally diverse aldehydes and ketones have been successfully fluorinated with DAST. These include acyclic, cyclic, and aromatic compounds. Elimination does occur to a certain extent when aldehydes and ketones are fluorinated and olefinic by-products are also observed in these instances.

While the DAST compounds have shown versatility in effecting deoxofluorinations, there are several well recognized limitations associated with their use. The compounds can decompose violently and while adequate for laboratory synthesis, they are not practical for large scale industrial use. In some instances, undesirable by-products are formed during the fluorination process. Olefin elimination by-products have been observed in the fluorination of some alcohols. Often, acid-catalyzed decomposition products are obtained. The reagent's two step method used for their synthesis renders these relatively costly compositions only suitable for small scale syntheses.

The DAST reagents are recognized as fluorinating reagents in U.S. Pat. Nos. 3,914,265 and 3,976,691. Additionally, Et-DAST and related compounds have been discussed in W. J. Middleton, New Fluorinating Reagents. Dialkylaminosulfur Fluorides, J. Org. Chem., Vol. 40, No. 5, (1975), pp 574–578. However, as reported by Messina, et al., Aminosulfur Trifluorides: Relative Thermal Stability, Journal of Fluorine Chemistry, 43, (1989), pp 137–143, these compounds can be problematic fluorinating reagents due to their tendency to undergo catastrophic decomposition (explosion or detonation) on heating. See also reports on this by J. Cochran, Laboratory Explosions, Chemical and Engineering News, (1979), vol. 57, No. 12, pp. 4 & 74; and W. T. Middleton, Explosive Hazards with DAST, Chemical and Engineering News, (1979), vol. 57, No. 21, p. 43. Difficulties with major amounts of by-products in the fluorination reaction is also noted. See also M. Hudlicky, Fluorination with Diethylaminosulfur Trifluoride and Related Aminofluorosulfuranes, Organic Reaction, Vol. 35, (1988), pp 513–553.

Further, Russian Inventor's Certificate No. 433,136 published Dec. 15, 1974 discloses sulfur dialkyl(alkylaryl) aminotrifluorides.

G. L. Hann, et. al., in Synthesis and Enantioselective Fluorodehydroxylation Reactions of (S)-2-(Methoxymethyl)pyrrolidin-1-ylsulphur Trifluoride, the First Homochiral Aminofluorosulphurane, J.Chem. Soc., Chem. Commun. (1989) pp 1650–1651, disclosed the aminosulfur trifluorides, (S)-2-(methoxymethyl)pyrrolidin-1-ylsulphur trifluoride and N-morpholinosulphur trifluoride as fluorinating reagents for 2-(trimethylsiloxy)octane.

The method and compositions of the present invention overcome the drawbacks of the prior art fluorinating reagents, including DAST, by providing more thermally stable fluorine bearing compounds which have effective fluorinating capability with far less potential of violent decomposition and attendant high gaseous by-product evolvement, with simpler and more efficient fluorinations, as will be set forth in greater detail below.

BRIEF SUMMARY OF THE INVENTION

The present invention is a method for the fluorination of a compound using a fluorinating reagent comprising contacting the compound with the fluorinating reagent under conditions sufficient to fluorinate the compound wherein the fluorinating reagent is an aminosulfur trifluoride composition having a structure with one or more:

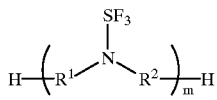

wherein m=1–5 and $R^1$ and $R^2$ are:
(1) when m=1, individually aryl or meta- or para-substituted aryl radicals in which the meta- or para-substitution is selected from the group consisting of normal and branched $C_{1-10}$, trifluoromethyl, alkoxy, aryl $C_{6-10}$, nitro, sulfonic ester, N,N-dialkylamino and halogens; or
(2) when m=1, individually aryl radicals which are fused or linked to one another; or
(3) when m=1, one of $R^1$ and $R^2$ is an aryl radical and the other is an at least 5 member saturated cyclic hydrocarbon radical having zero to three heteroatoms selected from the group consisting of oxygen, nitrogen and mixtures thereof; or
(4) when m=1, one of $R^1$ and $R^2$ is an aryl radical and the other is an at least 5 member saturated cyclic hydrocarbon radical having zero to three heteroatoms selected from the group consisting of oxygen, nitrogen and mixtures thereof wherein said cyclic hydrocarbon radical is fused to said aryl radical; or
(5) when m=1, together a cyclic ring having 2 to 10 carbon ring members and 1 heteroatom selected from the group consisting of oxygen, nitrogen and alkylated nitrogen wherein said ring has 1 to 2 alkoxyalkyl functionalities; or
(6) when m=1, together an unsaturated cyclic ring having 2 to 4 carbon ring members and one to three heteroatoms selected from the group consisting of oxygen, nitrogen, protonated nitrogen and alkylated nitrogen wherein said ring has one to three functional groups selected from hydrogen, normal and branched $C_{1-10}$ alkyl, haloalkyl, alkoxy, aryl halogen, cyano, nitro and amino; or
(7) when m=1, individually alkoxyalkyl radicals; or
(8) when m=1, one of $R^1$ and $R^2$ is alkoxyalkyl and the other is selected from the group consisting of alkyl and aryl radicals; or
(9) when m=2–5, $R^1$ is a single phenyl radical linked to each —$NSF_3$ radical and $R^2$ is an aryl radical having $C_6$ to $C_{10}$; or
(10) when m=2–5, $R^1$ and $R^2$ are individually divalent aryl radicals of $C_6$ to $C_{10}$ linked to adjacent —$NSF_3$ radicals except $R^1$ and $R^2$ are monovalent aryl radicals having $C_6$ to $C_{10}$ where $R^1$ and $R^2$ are linked to only one —$NSF_3$ radical; or
(11) when m=1, one of $R^1$ and $R^2$ is an aryl radical and the other is an alkyl radical of $C_{1-10}$.

Preferably, the compound being fluorinated is selected from the group consisting of alcohols, carboxylic acids, aldehydes, ketones, carboxylic acid halides, sulfoxides, phosphonic acids, sulfinyl halides, sulfonic acids, sulfonylhalides, silylhalides, silyl ethers of alcohols, epoxides, phosphines, thiophosphines, sulfides and mixtures thereof.

Preferably, the composition used as the fluorinating reagent has the structure:

wherein $R^{1-3, 6-8}$ are individually H, normal or branched alkyl $C_{1-10}$ or aryl $C_{6-10}$ and $R^{4-5}$ are $C_{2-10}$ normal or branched alkyl.

Alternatively, the composition used as the fluorinating reagent has the structure:

wherein $R^3$ and $R^6$ are individually $C_1$ to $C_{10}$ in a normal or branched chain alkyl and $R^4$ and $R^5$ are $C_{2-10}$ normal or branched alkyl.

More preferably, the composition used as the fluorinating reagent has the structure:

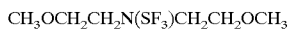

Preferably the fluorination is conducted in the presence of a solvent.

More preferably, solvent is selected from the group consisting of paraffins, halocarbons, ethers, nitriles, nitro compounds and mixtures thereof.

Preferably, the fluorination is conducted under anhydrous conditions.

Preferably, the fluorination is conducted at a temperature above the freezing point of said solvent and below the boiling point of said solvent.

Alternatively, when the compound is a ketone, the fluorination is catalyzed with at least a catalytic amount of a Lewis acid.

Preferably, the Lewis acid is selected from the group consisting of $BF_3$, $ZnI_2$, $TiCl_4$ and mixtures thereof.

Alternatively, when the compound is a ketone, at least a catalytic amount of HF is added to the fluorination.

Preferably the alcohol is selected from the group consisting of monofunctional and polyfunctional primary, secondary, tertiary and vinyl alcohols and mixtures thereof.

Preferably, the carboxylic acid is selected from the group consisting of aliphatic, aromatic and heterocyclic carboxylic acids and mixtures thereof.

Preferably, the aldehyde is selected from the group consisting of aliphatic, aromatic and heterocyclic aldehydes and mixtures thereof.

Preferably, the ketone is selected from the group consisting of aliphatic, aromatic and heterocyclic ketones and mixtures thereof.

Preferably, the carboxylic acid halide is selected from the group consisting of aliphatic, aromatic and heterocyclic carboxylic acid halides of chlorine, bromine and iodine and mixtures thereof.

Preferably, the sulfoxide is selected from the group consisting of aliphatic, aromatic and heterocyclic sulfoxides having adjacent hydrogen atoms and mixtures thereof.

Preferably, the phosphonic acid is selected from the group consisting of aliphatic, aromatic and heterocyclic phosphonic acids and mixtures thereof.

Preferably, the sulfinyl halide is selected from the group consisting of aliphatic, aromatic and heterocyclic sulfinyl halides of chlorine, bromine and iodine and mixtures thereof.

Preferably, the sulfonic acid is selected from the group consisting of aliphatic, aromatic and heterocyclic sulfonic acids and mixtures thereof.

Preferably, the sulfonyl halide is selected from the group consisting of aliphatic, aromatic and heterocyclic sulfonyl halides of chlorine, bromine and iodine and mixtures thereof.

Preferably, the silyl halide is selected from the group consisting of aliphatic, aromatic and heterocyclic silyl halides of chlorine, bromine and iodine and mixtures thereof.

Preferably, the silyl ether of alcohol is selected from the group consisting of silyl ethers of primary, secondary and tertiary alcohols and mixtures thereof.

Preferably, the epoxide is selected from the group consisting of aliphatic, aromatic and heterocyclic epoxide and mixtures thereof.

Preferably, the phosphine is selected from the group consisting of aliphatic, aromatic and heterocyclic phosphines and mixtures thereof.

Preferably, the thiophosphine is selected from the group consisting of aliphatic, aromatic and heterocyclic thiophosphines and mixtures thereof.

Preferably, the sulfide is selected from the group consisting of aliphatic, aromatic and heterocyclic sulfides with adjacent hydrogens and mixtures thereof.

In a preferred embodiment, the present invention is a method for the fluorination of a compound using a fluorinating reagent comprising an aminosulfur trifluoride composition comprising synthesizing the aminosulfur trifluoride composition with a secondary amine and $SF_4$ and without isolating said aminosulfur trifluoride composition, fluorinating said compound with said aminosulfur trifluoride composition.

Preferably, the synthesis is performed in the presence of a tertiary amine.

Preferably, the aminosulfur trifluoride is a dialkyl aminosulfur trifluoride, more preferably, diethylaminosulfur trifluoride.

BRIEF DESCRIPTION OF THE SEVERAL VIEWS OF THE DRAWINGS

Not Applicable

DETAILED DESCRIPTION OF THE INVENTION

A novel fluorination method using several novel aminosulfur trifluorides is presented in this invention. These compositions have been shown to be very efficient and useful for effecting deoxofluorination of alcohols and ketones. In addition, thermal analysis studies indicate that they should be much safer to use in the present fluorination method than the currently available dialkylaminosulfur trifluorides (DAST).

The simplicity of the method used for preparing the new aminosulfur trifluorides, as described hereafter, combined with their relative safety in use in the present invention should make this fluorination method attractive for large scale production of fluorinated products.

Fluorinating Reagents for the Present Method

The compositions useful in the present fluorination method are identified as follows by several general classes, including: Diaryl systems, alkoxyalkyl aminosulfur trifluorides and arylalkylaminosulfur trifluorides.

1. Diaryl Compositions

where Ar and Ar' are the same or different aryl groups (i.e., mixed compositions). The aryl groups can be mono or polynuclear, the latter encompassing isolated ring or fused-ring groups and each contemplates substituted aryl groups.

For example, when both groups are derived from benzene, the general formula is:

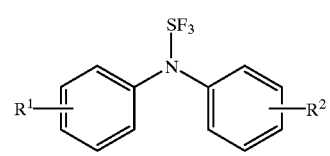

a) $R^1$ and $R^2$ represent one or more substituents (like or different). Examples provided (Table 1) for $R^1, R^2$=H, p-Cl, p-OCH$_3$, p-CH$_3$. These groups may be para or meta to the $NSF_3$ group. $R^1, R^2$ can additionally be OR (R=alkyl or aryl), Br, I, F, alkyl or aryl groups, $CF_3$, $NO_2$, $SO_3R$ (R=alkyl or aryl), $NR_2$ (R=alkyl or aryl). These groups may be ortho, meta or para to the $NSF_3$ group.

b) Aryl naphthyl compositions (Table 1)

c) Fused or linked diaryl compositions, e.g.,

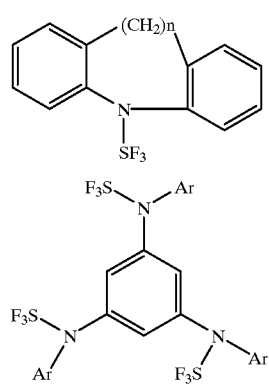

n=2 or more

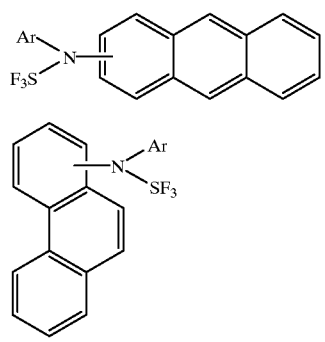

-continued

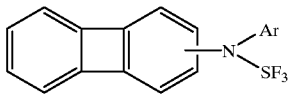

Furthermore, oligomeric or polymeric analogues may be used in which aromatic units are linked via the nitrogen of the NSF₃ group, such as:

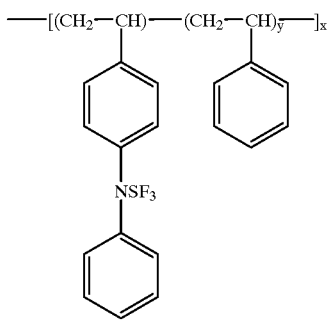

where y = 0–6 and x = 1–1000

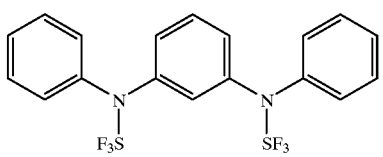

d) Heteroatom (O,N) containing aromatic compositions (branched or fused)

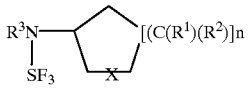

wherein $R^3$ is an aryl radical of $C_6$ to $C_{10}$, n=1–5, $R^1$ and $R^2$ are individually H or alkyl $C_{1-10}$ and X=zero to three ring element substitutions at any available position on the ring of O or $NR^4$ where $R^4$=H, normal or branched alkyl $C_{1-10}$.

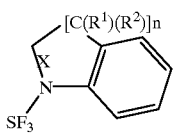

wherein $R^1$ and $R^2$=individually H or normal or branched alkyl $C_{1-10}$. n=1–5 and X=zero to three ring element substitutions at any available position on the ring of O or $NR^3$ where $R^3$=H, normal or branched alkyl $C_{1-10}$.

One of the aromatic ring groups attached to the N—SF₃ group may be 5-membered or greater and contain heteroatoms such as O(1–3) or N(1–3). The heteroatom-containing ring may be branched from the N—SF₃ group or fused to the other aromatic ring (Ar).

2. Alkoxyalkylamine Compositions a)
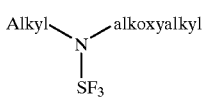

Table 5 b)
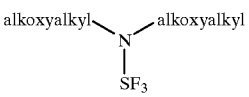

Table 5 c)
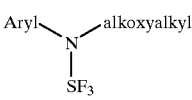

Table 5

Alkyl=normal or branched $C_{1-10}$. Alkoxyalkyl=(a) —$R^1$—O—$R^2$, where $R^1$ is $C_{2-10}$ normal or branched alkyl and $R^2$ is $C_{1-10}$ normal or branched alkyl or (b) —($R^3$—O)$_n$-$R^2$, where $R^2$ is $C_{1-10}$ normal or branched alkyl and $R^3$ is $C_{2-3}$ normal or branched alkyl and n=1–10.

d) Alkoxyalkyl branched from ring compositions containing NSF₃

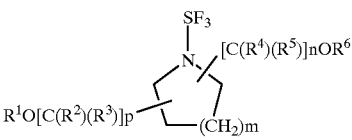

wherein $R^1$ and $R^6$ are individually normal or branched alkyl $C_{1-10}$, $R^{2-5}$, are individually H or normal or branched alkyl $C_{1-10}$, m=1–10, n=1–10, and p=1–10.

e) Alkoxyalkyl branched heteroatom ring compositions containing NSF₃

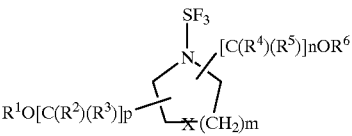

wherein $R^1$ and $R^6$ are individually normal or branched alkyl $C_{1-10}$, $R^{2-5}$, are individually H, or normal or branched alkyl $C_{1-10}$, m=1–10, n=1–10, and p=1–10, and X=a ring element substitution at any available position of the ring of O or $NR^7$ where $R^7$=H, normal or branched alkyl $C_{1-10}$.

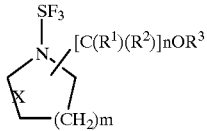

where m=1–10, n=1–10, $R^1$ and $R^2$=individually H, or normal or branched alkyl $C_{1-10}$, $R^3$=normal or branched alkyl $C_{1-10}$ and X=a ring element substitution at any available position of the ring of O, $NR^4$ where $R^4$=normal or branched alkyl $C_{1-10}$.

3. Arylalkylaminosulfur trifluorides

N-methyl, N-phenyl aminosulfur trifluoride exemplifies this group.

A preferred class of deoxofluorination reagents has the general structure:

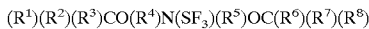

$(R^1)(R^2)(R^3)CO(R^4)N(SF_3)(R^5)OC(R^6)(R^7)(R^8)$ wherein $R^{1-3, \; 6-8}$ are individually H, normal or branched alkyl $C_{1-10}$ or aryl $C_{6-10}$ and $R^{4-5}$ are normal or branched $C_{2-10}$. A more specific class of preferred deoxofluorination reagents has the general structure:

$R^3OR^4N(SF_3)R^5OR^6$ wherein $R^3$ and $R^6$ are individually $C_1$ to $C_{10}$ normal or branched chain, $R^{4-5}$ are $C_{2-10}$ normal or branched alkyl. More specifically the deoxofluorination reagent has the specific structure:

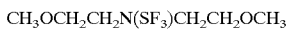

$CH_3OCH_2CH_2N(SF_3)CH_2CH_2OCH_3$

For the purpose of this invention the following definitions are provided. Alkyl shall mean normal and branched carbon radicals up to ten carbons. Aryl shall mean six and ten member carbon rings having aromatic character. Fused aryl shall mean aromatic rings containing two common carbon atoms. Linked aryl shall mean aromatic rings joined together by a bond from a carbon atom of one ring to a carbon atom of another ring. Heteroatoms shall mean oxygen and/or nitrogen in a carbon membered radical. Para-substitution on an aryl ring shall include H, p-Cl, p-OCH$_3$, p-CH$_3$, OR (R=alkyl $C_{1-10}$ or aryl $C_{6-10}$), Br, I, F, alkyl $C_{1-10}$ or aryl $C_{6-10}$ groups, NO$_2$, SO$_3$R (R=H, alkyl $C_{1-10}$ or aryl $C_{6-10}$), NR$_2$ (R=H, alkyl $C_{1-10}$ or aryl $C_{6-10}$). Alkoxyalkyl typically means an oxygen bridging two alkyl groups, but it is also contemplated to include polyethers, such as: —O(—RO)$_n$R' where R and R' are $C_{1-3}$ alkyl and n=1–10.

To develop thermally stable aminosulfur trifluorides for the fluorination method of the present invention, the inventors considered compositions which would not produce gaseous by-products on decomposition. The production of HF via abstraction of acidic protons in the vicinity of the N—SF$_3$ group by fluoride ion is believed to be one factor which contributes to the instability of the dialkylaminosulfur trifluorides. Consequently, compositions lacking such protons are attractive candidates for the present invention, although compositions with such protons can be useful. In order to circumvent the thermal instability which results from molecular disproportionation of dialkylaminosulfur trifluoride, the inventors prepared compositions which possess sterically demanding groups attached to the N—SF$_3$ function. Aminosulfur trifluorides with a highly electron deficient nitrogen bonded to the SF$_3$ group are also appropriate since molecular disproportionation will be less significant in these compositions.

The diaryl, arylalkyl and alkoxyalkylaminosulfur trifluorides fulfill most of the structural requirements for a thermally stable product for a fluorination method, such as deoxofluorination. The preparation and reactions of these compositions are described below.

An attempted synthesis of diphenylaminosulfur trifluoride by the conventional reaction route of the N-trimethylsilyl derivative of diphenylamine with SF$_4$ proved to be difficult. Only a small amount of product (<10% yield) was obtained in a reaction carried out at room temperature.

A synthetic route to dialkyl and arylalkylaminosulfur trifluorides described in Russian Inventor's Certificate No. 433,136 was used in which a secondary (2°) amine is reacted with SF$_4$ in ethyl ether containing triethylamine for the preparation of several novel diarylaminosulfur trifluorides. This simple one-step process (as opposed to the two-step method via a silyl amine) afforded a virtual quantitative yield of products at temperatures ranging from −10° C. to room temperature. Table 1 summarizes the diaryl compositions which were prepared by this method. The procedure proved to be particularly useful for the preparation of diarylaminosulfur trifluorides bearing both electron withdrawing and electron donating groups at the para position of the aromatic rings. The sterically hindered N-phenyl-N-naphthyl-amine was successfully converted to the diarylaminosulfur trifluoride at room temperature. However, the preparation of diarylaminosulfur trifluorides bearing substituent groups at the ortho position of the aromatic ring proved to be more difficult. None of the desired products were obtained in reactions carried out at −10° C. or room temperature with either 2,2'-dimethyl-diphenylamine or 2,2'-dimethoxy-diphenylamine. Instead only starting material was recovered after several hours (3–24 h) of reaction time. The steric hindrance imposed by the adjacent substituent groups on the aromatic ring seems to be significant in these compositions.

Aminosulfur trifluorides derived from relatively electron deficient diarylamines were found to be relatively unstable. In an attempted preparation of 4,4'-dichloro-diphenyl aminosulfur trifluoride, the amine was reacted with SF$_4$ in ethyl ether/triethylamine (Et$_2$O/TEA) at 0° C. After work-up a light yellow solid was isolated. This solid product darkened considerably on standing at room temperature (<1 h) forming 4-chlorophenyl iminosulfur difluoride as the principal decomposition product.

The aminosulfur trifluoride is synthesized by reaction of a secondary amine with SF$_4$ in a non-aqueous solvent that will not react chemically with SF$_4$ or the aminosulfur trifluoride product. Examples include ethers, e.g., ethylether (Et$_2$O), tetrahydrofuran (THF), halogenated hydrocarbons, e.g., CH$_2$Cl$_2$, freons, hydrocarbons, e.g., toluene, hexane, tertiary amines, liquid SO$_2$ and supercritical CO$_2$.

The reaction can be carried out at temperatures ranging from −90° C. or the freezing point of the solvent to the boiling point of the solvent.

The reaction mixture may be homogenous or heterogenous.

The secondary amine is represented by $R^1R^2NH$. $R^1$=alkyl (cyclic or non-cyclic, with or without heteroatoms), aryl, or alkoxyalkyl. $R^2$=alkyl (cyclic or non-cyclic, with or without heteroatoms), aryl or alkoxyalkyl. $R^1$ may or may not be the same as $R^2$.

The tertiary amine is represented by $R^1R^2R^3N$. $R^1$, $R^2$ or $R^3$=alkyl (cyclic or non-cyclic, with or without heteroatoms), or aryl. This includes tertiary amines which contain the N-atom in a ring, e.g., N-methylpiperidine or in a chain, e.g., triethylamine. It also includes tertiary amines which contain the N-atom at a bridge-head, e.g., quinuclidine or triethylene diamine and in fused rings, e.g., diazabicycloundecane (DBU). Compounds containing >1, tertiary amine group in the molecule can also be used. The tertiary amine could also function as the reaction solvent. Examples of specific amines employed for the synthesis of $R_2NSF_3$ reagents should also be effective for the in situ process described below.

No aminosulfur trifluoride product was obtained when pyridine or 3-methylpyridine was used instead of a tertiary amine; however, more basic pyridines than the latter are expected to be useful.

No aminosulfur trifluoride product was obtained when NaF or CsF was used instead of a tertiary amine. Thus, its utilization in the process beyond simply acting as an HF acceptor is an essential feature of the invention.

The substrate for fluorination may be an alcohol, an aldehyde, ketone, carboxylic acid, aryl or alkyl sulfonic acid, aryl or alkyl phosphonic acid, acid chlorides, silyl chlorides, silyl ethers, sulfides, sulfoxides, epoxides, phosphines and thiophosphines.

Water or a low molecular weight alcohol ($CH_3OH$, $C_2H_5OH$, etc.) may be added to hydrolyze the intermediate sulfinyl fluoride for disposal and to generate the starting secondary amine.

The fluorinated product may be separated from the aqueous acidic mixture by extraction into a water immiscible organic solvent.

The desired product may be distilled and thus isolated from the crude reaction mixture.

TABLE 1

Preparation of Diarylaminosulfur trifluorides from $SF_4$ and Diarylamines

| Starting Material | Reaction Conditions | Product (Yield) |
|---|---|---|
| 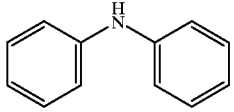 1 | $SF_4$ $Et_2O$, or THF, TEA −10° C., 3 h | 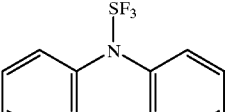 2 (quantitative) |
| 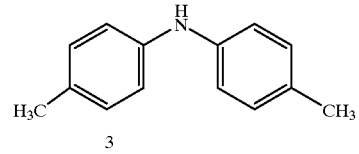 3 | $Et_2O$, or THF −10° C., 3 h | 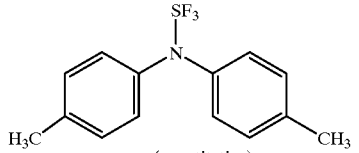 4 (quantitative) |
| 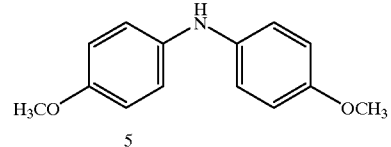 5 | $Et_2O$, or THF −10° C., 3 h | 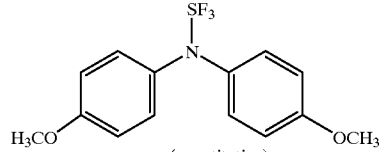 6 (quantitative) |
| 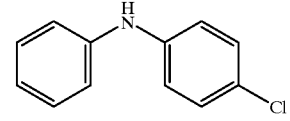 7 | $Et_2O$, or THF −10° C., 3 h | 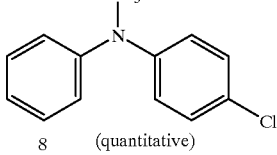 8 (quantitative) |
| 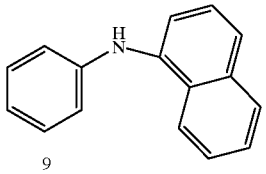 9 | $Et_2O$, or THF −10° C., 3 h | 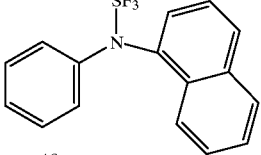 10 (quantitative) |

TABLE 1-continued

Preparation of Diarylaminosulfur trifluorides from SF₄ and Diarylamines

| Starting Material | Reaction Conditions | Product (Yield) |
|---|---|---|
| 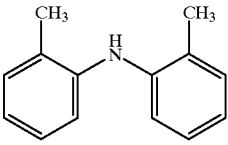<br>11 | THF<br>−78°–RT, 3 h | Starting material |
| 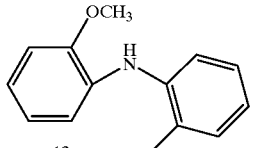<br>12 | Et₂O,<br>−78°–RT, 3 h | Starting material |
| 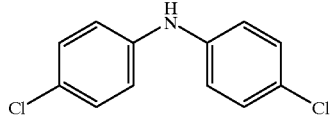<br>13 | Et₂O,<br>−78°–RT, 3 h | 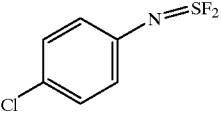<br>14 |

Saturated indoles (26, 28, Table 2) afford good yields of the corresponding aminosulfur trifluorides on reaction with SF₄ in Et₂O/TEA at −78° C. These compounds which appeared to be stable on initial preparation decomposed rapidly on storage (<3 days).

TABLE 2

Reaction of SF₄ with heterocyclic amines in Et₂O/TEA

| Starting material | Reaction Conditions | Product (yield) |
|---|---|---|
| 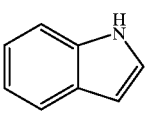<br>24 | SF₄, Et₂O, TEA<br>−78° C. to −10° C. | Tarry reaction product. No SF₃ derivative |
| 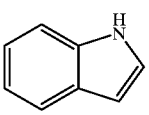<br>25 | SF₄, Et₂O, TEA<br>−78° C. to −10° C. | Tarry reaction product. No SF₃ derivative |
| 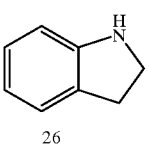<br>26 | SF₄, Et₂O, TEA<br>−78° C. to −10° C. | 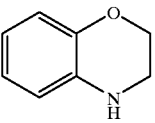<br>27<br>quantitative |

TABLE 2-continued

Reaction of SF₄ with heterocyclic amines in Et₂O/TEA

| Starting material | Reaction Conditions | Product (yield) |
|---|---|---|
| 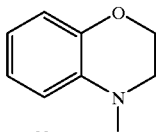<br>28 | SF₄, Et₂O, TEA<br>−78° C. to −10° C. | (structure 29)<br>29<br>quantitative |

Russian Inventor's Certificate No. 433,136 reported the preparation of N-ethyl-N-phenylaminosulfur trifluoride in 78% yield by reaction of N-ethyl-N-phenylamine with SF₄ in Et₂O containing tertiary (3°) amines. The present inventors confirmed these results and extended the method to the preparation of the N-methyl analog (Table 3). The arylalkyl amines were much more reactive towards SF₄ than the diarylamines and the reactions were completed at −78° C. with quantitative formation of products. The N-ethyl-N-phenyl aminosulfur trifluoride was not identified as a flu orinating agent. However, the present inventors found that this compound and related arylalkylaminosulfur trifluorides are very advantageous in deoxofluorination reactions, as set forth below.

TABLE 3

Preparation of arylalkyl aminosulfur trifluorides

| Starting material | Reaction conditions | Product (yield) |
|---|---|---|
| PhN(H)CH$_3$ 30 | SF$_4$, Et$_2$O, TEA −78° C., 1 h | PhN(SF$_3$)CH$_3$ 31 quantitative |
| PhN(H)C$_2$H$_5$ 32 | SF$_4$, Et$_2$O, TEA −78° C., 1 h | PhN(SF$_3$)C$_2$H$_5$ 33 quantitative |

It has been further determined that dialkylaminosulfur trifluorides that contain an oxygen atom in the vicinity of the SF$_3$ group possess enhanced thermal stability. The aminosulfur trifluorides with the highest reported decomposition temperatures are N-morpholinosulfur trifluoride and (S)-2-(methoxyethyl) pyrrolidin-1-yl-sulfur trifluoride. The increased thermal stability of these compounds may result from coordination of the electron-rich oxygen atom with sulfur affording a conformationally rigid structure. However, the inventors found that (S)-2-(methoxyethyl) pyrrolidin-1-yl-sulfur trifluoride was a poor fluorinating reagent for deoxofluorination of cyclooctanol, as reported below, and N-morpholino sulfurtrifluoride decomposes with the evolution of large quantities of gas (i.e., explosively). See Table 5.

The preparation of aminosulfur trifluorides by reaction of the amine with SF$_4$ in Et$_2$O/TEA was successfully applied to the preparation of several alkoxyalkylaminosulfur trifluorides (Table 4). These include compositions bearing one or two methoxy groups. The reactions of the precursor amines with SF$_4$ were quite rapid at −78° C. affording high yields of products.

TABLE 4

Preparation of alkoxyalkyl aminosulfur trifluorides

| Starting material | Reaction conditions | Product (Yield) |
|---|---|---|
| PhN(H)CH$_2$CH$_2$OMe 34 | SF$_4$, Et$_2$O, TEA −78° C., 1 h | PhN(SF$_3$)CH$_2$CH$_2$OMe 35 quantitative |
| CH$_3$NHCH$_2$CH$_2$OMe 36 | SF$_4$, Et$_2$O, TEA −78° C., 1 h | CH$_3$N(SF$_3$)CH$_2$CH$_2$OMe 37 quantitative |
| 2-(methoxymethyl)pyrrolidine 38 | SF$_4$, Et$_2$O, TEA −78° C., 1 h | 1-(SF$_3$)-2-(methoxymethyl)pyrrolidine 39 quantitative |
| MeOCH$_2$CH$_2$NHCH$_2$CH$_2$OMe 40 | SF$_4$, Et$_2$O, TEA −78° C., 1 h | MeOCH$_2$CH$_2$N(SF$_3$)CH$_2$CH$_2$OMe 41 quantitative |

Thermal analysis studies of the newly synthesized aminosulfur trifluorides and dialkylaminosulfur trifluorides (DAST) were performed on a Radex instrument, available from Systag of Switzerland. The instrument is similar to ASTM E476-87. The instrument operates at a constant heating rate (0.5 to 2.0° C./min.) and measures heat flux into or out of a sample, in the form of a temperature difference between sample and inert reference and also the system's total internal pressure. This provides a measure of the onset of exothermic decomposition. The results of these studies provide useful information about the relative thermal stabilities of these compositions. The decomposition temperature and the quantity of gas (resultant gas pressure) produced on decomposition are important indicators of the safety in use of the compositions.

Table 5 summarizes the results of the Radex thermal analysis studies and provides a listing of decomposition temperatures, pressure gain and gas produced on two bases for the decomposition of diaryl, dialkyl, arylalkyl, and alkoxyalkylaminosulfur trifluorides (300 mg). Higher decomposition temperatures were recorded for the dialkyl compositions. Among the newly synthesized compositions, the alkoxyalkylaminosulfur trifluorides decomposed at higher temperatures than the arylalkyl and diaryl compositions.

TABLE 5

Thermal analysis of aminosulfur trifluorides by Radex

| Composition | Decomposition Temp. ° C. | Pressure Gain on Decomposition (psia) | Gas Produced (psia/mmol |
|---|---|---|---|
| $Et_2NSF_3$ | 128 | 101 | 13 |
| Me2NSF3 | 126 | 96.6 | 33 |
| 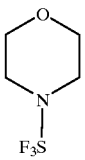 | 151 | 98.2 | 22 |
| 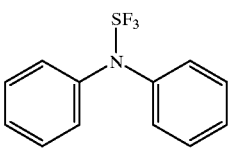 2 | 68 | 8.9 | 3 |
| 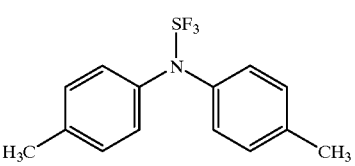 4 | 55 | 7.4 | 2 |
| 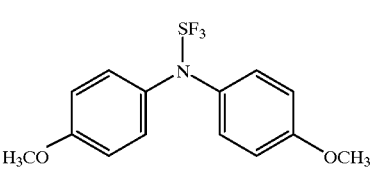 6 | 87 | 23.3 | 8 |
| 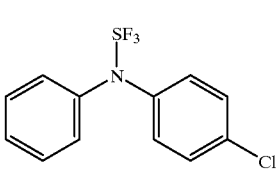 8 | 95 | 0 | 0 |

TABLE 5-continued

Thermal analysis of aminosulfur trifluorides by Radex

| Composition | Decomposition Temp. °C. | Pressure Gain on Decomposition (psia) | Gas Produced (psia/mmol |
|---|---|---|---|
| 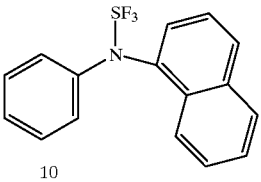<br>10 | 109 | 10.0 | 3 |
| 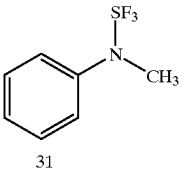<br>31 | 91 | 9.9 | 3 |
| 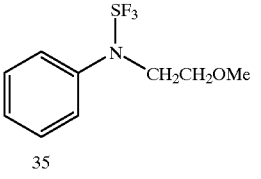<br>35 | 66 | 0 | 0 |
| $CH_3N(SF_3)CH_2CH_2OMe$<br>37 | 104 | 1.5 | 0 |
| 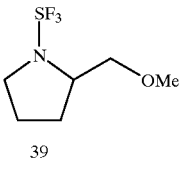<br>39 | 116 | 16.5 | 5 |
| $MeOCH_2CH_2N(SF_3)CH_2CH_2OMe$<br>41 | 108 | 0 | 0 |

A comparison of the pressure gain on decomposition indicates that the dialkyl aminosulfur trifluorides produced a significantly larger quantity of gas as compared to the other compositions. Most of the diaryl compositions produced a relatively small quantity of gas. However, N-4-chlorophenyl-N-phenylaminosulfur trifluoride was found to be remarkably stable in this regard producing no gas on decomposition. The arylalkyl compositions produced some gas on decomposition, but the alkoxyalkylaminosulfur trifluorides evolved essentially no gas at the conditions of these tests. However, the most significant factor demonstrated by the data in Table 7 is the amount of gas produced per mmol of deoxofluorination reagent tested. This is a measure of the potential for dangerous results based upon explosion of the reagent for a normalized amount of each reagent for comparison purposes. The reagents of the present invention showed significant improvement over the prior art compositions.

These results indicate that the novel aminosulfur trifluorides prepared should be much safer to use than the previously known DAST compounds. The more stable N-4-chlorophenyl-N-phenylaminosulfur trifluoride and the alkoxyalkylaminosulfur trifluorides should be especially suitable for scale-up and large scale use.

NMR spectra were obtained on a Bruker CP-300FT spectrometer operating at 282.4 MHz ($^{19}F$), 300.13 MHz ($^{1}H$). Chemical shifts were referenced to neat $CFCl_3$($^{19}F$) and $CHCl_3$(H).

G.C.M.S. Spectra were recorded on a HP 5890 Series 11 G.C. and 5972 series mass selective detector with a HP-1 column.

All compositions in subparagraphs (1) through (10) of the Summary of the Invention are novel. There is one example in the literature of a composition that exemplifies subparagraph (11): N-ethyl-N-phenyl aminosulfurtrifluoride. It was prepared by L. N. Markovskii, et al (USSR patent, 1974, No(II) 433136), but it was never used, or suggested for use, as a fluorinating agent. Other members of this class (e.g., the N-methyl-N-phenyl analog) were prepared and used. (S)-2-(methoxymethyl) pyrrolidin-1-yl-sulfur trifluoride (compound 39 in Table 5) was reported in the literature. It was only employed in the fluorination of silylethers. No indication or suggestion was given that the compound should be generally useful for the replacement of certain oxygen atoms in organic compounds, i.e., for the deoxofluorination of alcohols, ketones, aldehydes, etc. In fact, in the experimental work of the present invention, the deoxofluorination of alcohols by this compound afforded much less yield than is obtained by fluorination using our new compositions of aminosulfurtrifluorides. For example, only a 17% yield of cyclooctyl fluoride was obtained on fluorination of cyclooctanol with compound 39. In contrast yields in excess of 70% were obtained on fluorination of cyclooctanol with the novel aminosulfur trifluorides under the same reaction conditions. It is expected that the fluorination of a silyl ether (which proceeds via the formation of a reactive oxygen anion, R—O⁻) will be more facile than reaction of the corresponding alcohol ROH with the —SF$_3$ compound.

The known N,N-dialkylaminosulfurtrifluorides, R$_2$NSF$_3$, (e.g., (C$_2$H$_5$)$_2$SF$_3$ (DAST), and including those which contain O as a heteroatom such as N-morpholino sulfurtrifluoride, as well as the, bis(N,N-dialkylamino)-sulfur difluorides, are well known, useful reagents for effecting the replacement of certain oxygen and halogen (Cl, Br, I) atoms in various classes of organic compounds with fluorine. The present inventors have found that the aminosulfur trifluoride compounds of subparagraphs (1) to (11) are generally safer to use, and can perform the oxygen and halogen replacement chemistry with significant improvements in reaction selectivity and yield of the desired fluoro product.

All compositions under subparagraphs (1) to (11) of the Summary of the Invention, are safer to use than the dialkylaminosulfurtrifluorides, on the basis of quantifiable thermal decomposition criteria, set forth in Table 5. These are: onset temperature of self-heating, and rate and extent of pressure increase, as measured by Radex instrumentation, and in some cases by accelerated rate calorimetry (ARC) measurements. It is believed that the most discerning criterion for safety in use is the pressure gain of volatiles upon decomposition, which may be qualitatively related to potential explosivity. Note that the dialkylaminosulfur-trifluorides (first 3 entries in Table 5) have far larger values of pressure gained, as compared to compounds in subparagraphs (1) to (11).

In general, with compounds of subparagraphs (1) to (11), higher yields and selectivities to the desired fluoroproducts were realized, for alcohol and ketone substrates, as compared to those realizable under the same conditions with the dialkylaminosulfurtrifluorides.

For the fluorination of cyclooctanol (a model alcohol) with DAST, W. M. Middleton reported, for the formation of cyclooctyl fluoride, a yield of 70% and 30% of a cyclooctene elimination product. (Ref. *J. Org. Chem.* 40, 574 (1975) ). The data of the present invention on this reaction of cyclooctanol, done under the same conditions, is in Table 6. For diphenylaminosulfurtrifluoride (first entry in Table), the yield and selectivity are comparable to those of DAST. However, all the other reagents defined in subparagrahs (1) to (11) of the Summary of the Invention offer significantly higher yields of the desired fluoro products, and higher selectivities (less elimination products).

For the fluorination of 4-t-butylcyclohexanone, a model ketone, with DAST a 67% yield of 1,1-difluoro-4-t-butylcyclohexanone was obtained. The remainder, (33%) consisted of many other fluorinated by-products including the vinyl fluoride: 1-t-butyl-4-fluoro-3-cyclohexene. Data for the same ketone fluorination reaction conducted with compounds of subparagraphs (1) to (11) are presented in Table 7. For all these compounds, the only products seen (by NMR) are the 1,1-difluoro-4-t-butylcyclohexane and the vinyl fluoride compound. The reactions were remarkably (and surprisingly) clean. The desired difluoro compound is always produced in a higher yield than was seen for DAST, the remainder being only the vinyl fluoride. The difluoro to Vinyl Fluoride ratio, e.g., 96:4 for Ph$_2$NSF$_3$ cited in Table 7, is thus equivalent to a 96% yield of the required difluoro product).

Synthesis of the novel and more stable fluorinating reagent compositions used in the fluorination method of the present invention will now be set forth with regard to the following examples.

EXAMPLE 1

Synthesis of Aminosulfur Trifluorides

A 3-neck, 250 mL round-bottom flask was equipped with a magnetic stirring bar, a N$_2$ inlet tube attached to dry ice condenser, a SF$_4$ gas inlet tube connected to a metal vacuum line manifold and a pressure equalized dropping funnel. The solvent (Et$_2$O or THF, 75 mL) was introduced into the flask via the dropping funnel and a 2° amine, corresponding to the products as specified below (25.0 mmol), dissolved in the solvent (Et$_2$O or THF, 25 mL) and triethylamine (3.50 mL, 25.0 mmol) were added to the dropping funnel. The condenser was cooled to −78° C. with dry ice/acetone and the solvent was cooled in like manner. A 1 liter ballast in the manifold was filled with SF$_4$ from a metal cylinder to produce a pressure of 18 psia and SF$_4$ (13 psia, 37 mmol) was introduced into the flask. The residual SF$_4$ in the ballast was pumped through a soda-lime trap. The solution of 2° amine in Et$_2$O/TEA was then added dropwise to the SF$_4$ solution and stirred. The −78° C. bath was replaced by a −10° C. bath and the mixture was stirred for 3 h. After cooling to −78° C., excess SF$_4$ was pumped out of the solution through a soda-lime trap and the solution was brought to room temperature. When Et$_2$O was used as solvent, an H-tube was attached to the flask and the solvent decanted into one arm of the H-tube. This was followed by filtration of the solution to remove precipitated TEA•HF. The filtrate was then evaporated in-vacuo. After the solvent was completely removed, the H-tube was taken into a dry-box and the product was transferred to a Teflon bottle. When THF was used as solvent, an in-vacuo evaporation of the solvent was first carried out and the residue was redissolved into Et$_2$O and further processed as above $^1$H and $^{19}$F NMR of samples were done in teflon NMR tubes.

The following compositions were obtained via this procedure: diphenylaminosulfur trifluoride (2), $^1$H NMR (CDCl$_3$)δ 7.5–7.3 (m, 10H), $^{19}$F NMR (CDCl$_3$)δ 69.5 (d, 2F), 31 (t, 1F)•4,4'-dimethyl-diphenylamino-sulfur trifluoride (4)•$^1$H NMR (CDCl$_3$)δ 7.35–7.10 (m, 8H), 2.35 (s, 6H)•$^{19}$F NMR (CDCl$_3$)δ 68.25 (d, 2F), 32.0 (t, 1 F)•4,4'-dimethoxy-diphenylaminosulfur trifluoride (6)•$^1$H NMR (CDCl$_3$)δ 7.25 (d, 4H), 7.35 (d, 4H), 3.8 (s, 6H)•$^{19}$F NMR (CDCl$_3$)δ 68.5 (s, br, 2F), 31.75 (s, br, 1F)•N-4-chlorophenyl-N-phenylaminosulfurtrifluoride (8)•$^1$H NMR (CDCl$_3$)δ 7.5–7.25 (m, 9H), $^{19}$F NMR (CDCl$_3$)δ 70 (d, 2F), 31 (t, 1F)•N-naphthyl-N-phenyl-aminosulfur trifluoride (10) •$^1$H NMR (CDCl$_3$)δ 8.4 (d, 0.66H), 8.15 (d, 0.34H), 7.9–6.8 (m, 11H), $^{19}$F NMR (CDCl$_3$)δ 71, 66.5 (2(d) 0.66F), 70, 67.5 (2(d), 134F) 33 (t, 1F)•Indolineaminosulfur trifluoride (27)•$^1$H NMR (CDCl$_3$)δ 7.4 (d, 1H), 7.2 (dd, 2H), 7.0 (d, 1H), 4.3 (t, 2H), 3.1 (t, 2H)•$^{19}$F NMR (CDCl$_3$)δ 60 (br, s, 2F), 20 (br, s, 1F)•3,4-dihydro-2H-1,4-benzoxazinesulfur trifluoride (29)•$^1$H NMR (CDCl$_3$)δ 7.3–7.1 (m, 2H), 6.8–7.1 (m, 2H), 4.5–4.3 (t, 2H), 4.2–3.9 (t, 2H)•$^{19}$F NMR (CDCl$_3$)δ 63 (br, s, 2F) 11 (br, s, 1F). N-methyl-N-phenylaminosulfur trifluoride (31)•$^1$H NMR (CDCl$_3$)δ 7.5–7.3 (m, 3H), 7.3–7.0 (m, 2H) 3.4 (s, 3H) $^{19}$F NMR (CDCl$_3$)δ 64 (2F)δ 26 (1F)•N-ethyl-N-phenyl aminosulfur trifluoride (33)$^{25}$•N-2-methoxyethyl-N-phenylaminosulfur trifluoride (35) $^1$H NMR (CDCl$_3$)δ 7.5–7.35 (m, 3H), 7.35–7.20 (m, 2H), 4.1–3.9 (m, 2H), 3.7–3.5 (m, 2H), 3.30 (s, 3H) $^{19}$F NMR (CDCl$_3$)δ 63 (br, s, 2F), 31.5 (br, s, 1 F)•N-2-methoxyethyl-N-methylaminosulfur trifluoride (37)•$^1$ H NMR (CDCl$_3$)δ 3.8–3.3 (m, 4H), 3.15 (s, 3H), 2.95 (s, 3H) $^{19}$F NMR (CDCl$_3$)δ 56 (s, br, 2F), 23 (s, br, 1F)•(S)-2-(methoxymethyl) pyrrolidin-1-yl sulfur trifluoride (39)$^{26}$•bis (2-methoxyethyl)aminosulfur trifluoride (41) $^1$H NMR (CDCl$_3$)•δ 3.5 (t, 4H), 3.15 (t, 4H), 3.05 (s, 6H) $^{19}$F NMR (CDCl$_3$)δ 55 (s, br, 2F) 28 (s, br. 1 F).

Present Fluorination Method with Novel Aminosulfur Trifluorides

The fluorination reactions of target compounds with the aminosulfur trifluorides are conducted by charging the reaction vessel with the substrate first then adding the aminosulfurtrifluoride or charging the vessel first with the aminosulfur trifluoride then adding the substrate. Alternatively, both may be charged simultaneously. Solvents may or may not be used. Solvents include materials which will not react with the aminosulfur trifluoride or substrate. These include hydrocarbons e.g. hexane, halocarbons e.g., CH$_2$Cl$_2$, ethers, such as diethyl ethe,r nitriles, such as acetonitrile, nitro compounds e.g. nitromethane.

The fluorination reactions are usually conducted under anhydrous conditions in metal, glass, plastic or ceramic vessels. The fluorination reaction temperature is conducted at any temperature between the freezing point of the solvent and the boiling point of the solvent. Pressure is usually not necessary and reactions are mostly carried out at ambient or autogeneous pressure.

The fluorination products can be separated from the reaction mixture and then purified by standard methods including distillation, chromatography, solvent extraction and recrystallization.

In general, with the aminosulfurtrifluoride compositions of the present invention higher yields and selectivities to the desired fluoroproducts were realized, for alcohol and ketone substrates, as compared to those realizable under the same conditions with the dialkylaminosulfurtrifluorides.

Fluorination of the 1°alcohol, phenethanol was also easily accomplished. For example reaction of this compound with Ph$_2$NSF$_3$ and (MeOCH$_2$CH$_2$)$_2$NSF$_3$ produce phenethyl fluoride in 60 and 68% yield respectively.

Fluorination of the 3°alcohol, ethyl-2-hydroxybutyrate with Ph(Me)NSF$_3$ afforded a 90% yield of ethyl-2-fluorobutyrate. Similar results were obtained with bis-methoxyethyl aminosulfur trifluoride. With the 3°alcohol, acetone cyanohydrin a 66% yield of 2-fluoro-2-methylpropionitrile was obtained on reaction with Ph(Me) NSF$_3$.

Aldehydes and ketones react with the aminosulfur trifluorides to effect a replacement of the oxygen atom by two fluorine atoms. For example benzaldehyde reacted with either Ph$_2$NSF$_3$ or (MeO CH$_2$CH$_2$)$_2$NSF$_3$ to produce benzal fluoride (PhCHF$_2$) in quantitative yields. The dialdehyde, terephthaldehyde reacted with Ph(Me)NSF$_3$ to afford a 95% yield of 1,'1,'4,'4'-tetrafluoro-p-xylene.after 16 h at room temperature in CH$_2$Cl$_2$. This product was obtained in 98% yield on reaction with (MeOCH$_2$CH$_2$)$_2$NSF$_3$ in refluxing CH$_2$Cl$_2$ after 5 h while an 86% yield was obtained on reaction with Ph(Me)NSF$_3$ in CH$_2$Cl$_2$ at room temperature after 69 h.

Other ketones also afforded the corresponding gem-difluoro product on reaction with the aminosulfur trifluorides. For example 4-carboethoxy cyclohexanone react with Ph(Me)NSF$_3$ and N-4-chlorophenyl-N-phenyl aminosulfur trifluoride to produce 1-carboethoxy-4,4-diflurocyclohexanone in CH$_2$Cl$_2$ in 70% and 95% yields respectively. Also a 30% yield of difluorocyclooctane was obtained on reaction of cyclooctanone with Ph$_2$NSF$_3$ at room temperature after 7 days in CH$_2$Cl$_2$.

When the compound is a ketone, at least a catalytic amount of HF can be added to the fluorination. The HF may be added as the neat liquid or gas or as an adduct with a base, as with HF•pyridine.

Carboxylic acids react with aminosulfur trifluorides to produce carboxylic acid fluorides. For example benzoic acid reacts with Ph$_2$NSF$_3$ to produce benzoyl fluoride in quantitative yield.

Carboxylic acid chlorides react with aminosulfur trifluorides to produce acid fluorides. For example (MeOCH$_2$CH$_2$)$_2$NSF$_3$ react with benzoic acid to generate benzoyl fluoride in quantitative yield.

Sulfoxides react with aminosulfur trifluorides to afford a-fluorosulfides. For example phenyl methyl sulfoxide gave fluoromethyl phenyl sulfide in 70% yield on reaction with (MeOCH$_2$CH$_2$)$_2$NSF$_3$.

Epoxides react with aminosulfur trifluorides to produce the corresponding vicinal difluoride. For example cyclohexene oxide reacts with bis(2-methoxyethyl)aminosulfur trifluoride in. CH$_2$Cl$_2$ containing a catalytic quantity of HF to afford 1,2-difluorocyclohexane in 33% yield.

It was found that the deoxofluorination of ketones by Ph(Me)NSF$_3$ are considerably accelarated in the presence of Lewis acids as catalysts. No such rate increase was observed with Et$_2$NSF$_3$ (prior art DAST). For example in the synthesis of 1-t-butyl-4,4-difluorocyclohexane from 4-t-butylcyclohexanone and Ph(Me)NSF$_3$ a quantitative yield was obtained in the presence of 0.1 equivalent of BF$_3$.OEt$_2$ after 16 h. In the absence of BF$_3$.OEt$_2$ the reaction took 69 h for complete conversion of the starting material to product. A similar accelaration of this reaction was observed with Znl$_2$ and TiCl$_4$. No increase in rate with added Lewis acids was observed when the fluorination of 4-t-butylcyclohexanone was carried out with $Et_2NSF_3$ (prior art DAST). These results indicate that $Ph(Me)NSF_3$ may be useful for fluorinating unreactive ketones.

In an examplary fluorination of the present invention, deoxofluorination of cyclooctanol with diarylaminosulfur trifluorides proceeds rapidly at −78° C. in $CH_2Cl_2$ to produce cyclooctylfluoride and cyclooctene with the former predominating (Table 6). Differing ratios of fluoride to olefin were observed with the various aromatic substituted trifluorides. The sterically hindered N-naphthyl-N-phenylaminosulfur trifluoride reacted quite slowly affording only a 10% conversion of starting material to products after 16 h at room temperature. A rapid conversion to the monofluoride was obtained with N-methyl-N-phenylaminosulfur trifluoride. Among the alkoxyalkyl compositions 35–41 (Table 4), the phenyl substituted aminosulfur trifluoride (35) proved to be the most reactive affording fluorination at −78° C. in 1 h as compared to the methyl and bisalkoxyalkyl compositions (37, 41, respectively) which required longer reaction times (~3 hr) at −78° C. to effect the same conversion.

EXAMPLE 2

Reaction of Cyclooctanol with the New Aminosulfur Trifluorides

A solution of cyclooctanol (128 mg, 1 mmol) in $CH_2Cl_2$ (3.0 mL) was added to a solution of aminosulfur trifluoride per Table 8 (1 mmol) in $CH_2Cl_2$ (2.0 mL) at −78° C. under $N_2$ in a 3-neck flask equipped with $N_2$ inlet, septum, and a magnetic stirring bar. The reaction was monitored by G.C.M.S. for disappearance of the starting material. On completion, the mixture was poured into satd. $NaHCO_3$ (25 mL) and after $CO_2$ evolution ceased, it was extracted into $CH_2Cl_2$ (3×15 mL), dried ($Na_2SO_4$), filtered and evaporated in vacuo to obtain the product as a mixture of cyclooctyl fluoride and cyclooctene. Flash chromatography on silica gel in hexane afforded the pure products.

The aminosulfur trifluoride is synthesized by reaction of a secondary amine with $SF_4$ in a non-aqueous solvent that will not react chemically with $SF_4$ or the aminosulfur trifluoride product. Examples include ethers, e.g., ethylether ($Et_2O$), tetrahydrofuran (THF), halogenated hydrocarbons, e.g., $CH_2Cl_2$, freons, hydrocarbons, e.g., toluene, hexane, tertiary amines, liquid $SO_2$ and supercritical $CO_2$.

The reaction can be carried out at temperatures ranging from −90° C. or the freezing point of the solvent to the boiling point of the solvent.

The reaction mixture may be homogenous or heterogenous.

The secondary amine is represented by $R^1R^2NH$. $R^1$=alkyl (cyclic or non-cyclic, with or without heteroatoms), aryl, or alkoxyalkyl. $R^2$=alkyl (cyclic or non-cyclic, with or without heteroatoms), aryl or alkoxyalkyl. $R^{-1}$ may or may not be the same as $R^2$.

The tertiary amine is represented by $R^1R^2R^3N$. $R^1$, $R^2$ or $R^3$=alkyl (cyclic or non-cyclic, with or without heteroatoms), or aryl. This includes tertiary amines which contain the N-atom in a ring, e.g., N-methylpiperidine or in a chain, e.g., triethylamine. It also includes tertiary amines which contain the N-atom at a bridge-head, e.g., quinuclidine or triethylene diamine and in fused rings, e.g., diazabicycloundecane (DBU). Compounds containing >1, tertiary amine group in the molecule can also be used. The tertiary amine could also function as the reaction solvent. Examples of specific amines employed for the synthesis of $R_2NSF_3$ reagents should also be effective for the in situ process described below.

No aminosulfur trifluoride product was obtained when pyridine or 3-methylpyridine was used instead of a tertiary amine; however, more basic pyridines than the latter are expected to be useful.

No aminosulfur trifluoride product was obtained when NaF or CsF was used instead of a tertiary amine. Thus, its utilization in the process beyond simply acting as an HF acceptor is an essential feature of the invention.

The substrate for fluorination may be an alcohol, an aldehyde, ketone, carboxylic acid, aryl or alkyl sulfonic acid, aryl or alkyl phosphonic acid, acid chlorides, silyl chlorides, silyl ethers, sulfides, sulfoxides, epoxides, phosphines and thiophosphines.

Water or a low molecular weight alcohol ($CH_3OH$, $C_2H_5OH$, etc.) may be added to hydrolyze the intermediate sulfinyl fluoride for disposal and to generate the starting secondary amine.

The fluorinated product may be separated from the aqueous acidic mixture by extraction into a water immiscible organic solvent.

The desired product may be distilled and thus isolated from the crude reaction mixture.

TABLE 6
Deoxofluorination of cyclooctanol
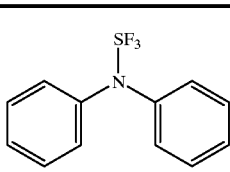
| Aminosulfur trifluoride | Reaction conditions | Ratio of cyclooctyl fluoride/ cycloctene |
|---|---|---|
| 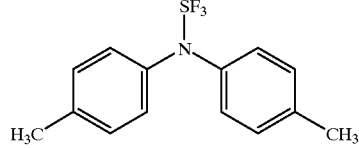<br>2 | $CH_2Cl_2$, −78° C.<br>1 h | 70:30 |
| 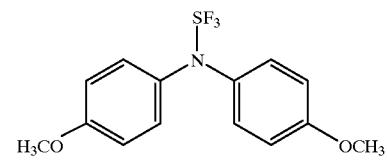<br>4 | $CH_2Cl_2$, −78° C.<br>1 h | 90:10 |
| 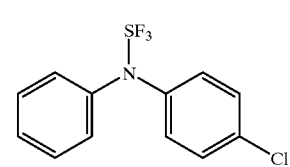<br>6 | $CH_2Cl_2$, −78° C.<br>1 h | 76:24 |
| 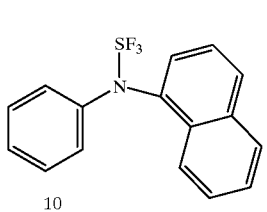<br>8 | $CH_2Cl_2$, −78° C.<br>1 h | 94:6 |
| 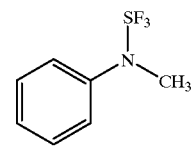<br>10 | $CH_2Cl_2$, RT<br>16 h, 10% conversion | |
| <br>31 | $CH_2Cl_2$, −78° C.<br>1 h | 99:1 |

TABLE 6-continued

Deoxofluorination of cyclooctanol

[Reaction scheme: cyclooctanol with OH reacts with R$_2$NSF$_3$ to give cyclooctyl fluoride (F) + cyclooctene]

| Aminosulfur trifluoride | Reaction conditions | Ratio of cyclooctyl fluoride/cyclooctene |
|---|---|---|
| [Structure: phenyl-N(SF$_3$)(CH$_2$CH$_2$OMe)] 35 | CH$_2$Cl$_2$, −78° C. 1 h | 90:10 |
| CH$_3$N(SF$_3$)CH$_2$CH$_2$OMe 37 | CH$_2$Cl$_2$, −78° C. 3 h | 85:15 |
| MeOCH$_2$CH$_2$N(SF$_3$)CH$_2$CH$_2$OMe 41 | CH$_2$Cl$_2$, −78° C. 3 h | 85:15 |
| [Structure: pyrrolidine-N(SF$_3$) with CH$_2$OMe substituent] 39 | CH$_2$Cl$_2$, −78° C. 8 h | 17:6 |
| (C$_2$H$_5$)$_2$NSF$_3$ | CCl$_3$F | 70:30 |

In contrast to the superior deoxofluorination of cyclooctanol for the reagents reported in Table 6, (S)-2-(methoxyethyl) pyrrolidin-1-yl-sulfur trifluoride was a poor deoxofluorination reagent for cyclooctanol. In a reaction carried out at −78° C. in CH$_2$Cl$_2$ for 8 h only 17% cyclooctyl fluoride was produced and 6% cyclooctene, as determined by nuclear magnetic resonance.

Table 6 summarizes the results obtained on fluorination of 4-t-butyl cyclohexanone with the aminosulfur trifluorides. All of the compositions examined except N-naphthyl-N-phenylaminosulfur trifluoride converted the ketone to a mixture of 4-t-butyl-difluorocyclohexane and 4-t-butyl-1-fluorocyclohexene, with the former predominating. The fluorination of this ketone was much slower than observed for the fluorination of cyclooctanol. A complete conversion to the fluorinated products required several days at room temperature in CH$_2$Cl$_2$. However, addition of a catalytic amount of HF (generated in-situ from EtOH) accelerated the rate of reaction considerably. The reaction time was reduced from several days to ~16 h when the diaryl, arylalkyl, and N-methoxyethyl-N-phenylaminosulfur trifluorides were reacted with 4-t-butylcyclohexanone in the presence of HF. The effect of HF on reaction rate was, however, less pronounced with the alkoxyalkyl aminosulfur trifluorides 37 and 41. A reasonable reaction time (40 h) for complete fluorination of the ketone with bis(methoxyethyl-aminosulfur trifluoride (41) was obtained when the reaction was carried out at 40° C.

EXAMPLE 3

Reaction of 4-t-Butylcyclohexanone with Aminosulfur Trifluorides

A solution of 4-t-butylcyclohexanone (1.0 mmol) in CH$_2$Cl$_2$ (3.0 mL) contained in a 25 mL teflon vessel equipped with a swagelok stopper, N$_2$ inlet tube, and stirring bar was treated with a solution of aminosulfur trifluoride per Table 9 (1.8 mmol) in CH$_2$Cl$_2$ (2.0 mL) at room temperature. EtOH (11 mg, 14 μL, 0.2 mmol) was added and the mixture was stirred at room temperature. The progress of the reaction was monitored by a G.C.M.S. On completion, the solution was poured into satd. NaHCO$_3$ and after CO$_2$ evolution ceased, it was extracted into CH$_2$Cl$_2$ (3×15 mL), dried (Na$_2$SO$_4$), filtered, and evaporated in vacuo to afford a mixture of 4-t-butyl-difluorocyclohexane and 4-t-butyl-1-fluorocyclohexene.

TABLE 7
Deoxofluorination of 4-t-butylcyclohexanone
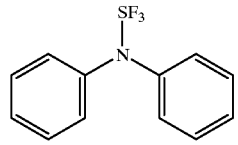
| Aminosulfur trifluoride | Reaction conditions | Ratio of cyclooctyl fluoride/ cycloctene |
|---|---|---|
| 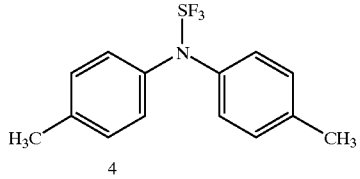<br>2 | CH$_2$Cl$_2$, −78° C.<br>1 h | 70:30 |
| 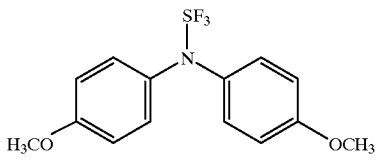<br>4 | CH$_2$Cl$_2$, −78° C.<br>1 h | 90:10 |
| 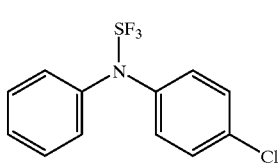<br>6 | CH$_2$Cl$_2$, −78° C.<br>1 h | 76:24 |
| 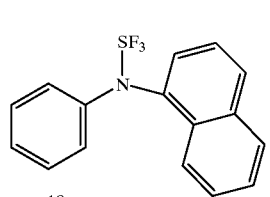<br>8 | CH$_2$Cl$_2$, −78° C.<br>1 h | 94:6 |
| 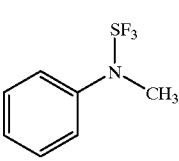<br>10 | CH$_2$Cl$_2$, RT<br>16 h, 10%<br>conversion | |
| <br>31 | CH$_2$Cl$_2$, −78° C.<br>1 h | 99:1 |

TABLE 7-continued

Deoxofluorination of 4-t-butylcyclohexanone

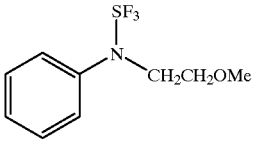

| Aminosulfur trifluoride | Reaction conditions | Ratio of cyclooctyl fluoride/ cycloctene |
|---|---|---|
| 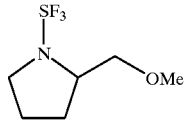<br>35 | $CH_2Cl_2$, $-78°$ C.<br>1 h | 90:10 |
| $CH_3N(SF_3)CH_2CH_2OMe$<br>37 | $CH_2Cl_2$, $-78°$ C.<br>3 h | 85:15 |
| $MeOCH_2CH_2N(SF_3)CH_2CH_2OMe$<br>41 | $CH_2Cl_2$, $-78°$ C.<br>3 h | 85:15 |
| 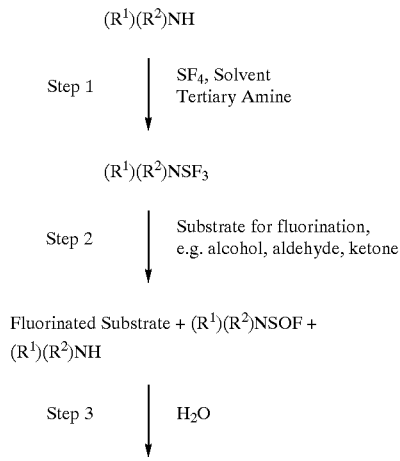<br>39 | $CH_2Cl_2$, $-78°$ C.<br>8 h | 17:6 |
| $(C_2H_5)_2NSF_3$ | $CCl_3F$ | 70:30 |

A convenient and economically attractive method for deoxofluorination of the alcohol (cyclooctanol) and ketone (4-t-butylcyclohexanone) was achieved by conducting the reaction in the medium used for preparation of the reagent, i.e., without isolating the aminosulfur trifluoride.

Schematic representation of the in-situ fluorination process:

$(R^1)(R^2)NH$

Step 1 | $SF_4$, Solvent
Tertiary Amine $(R^1)(R^2)NSF_3$

Step 2 | Substrate for fluorination,
e.g. alcohol, aldehyde, ketone

Fluorinated Substrate + $(R^1)(R^2)NSOF$ + $(R^1)(R^2)NH$

Step 3 | $H_2O$

Fluorinated Substrate + HF + $H_2SO_3$

Step 4 | Separation of Product

Fluorinated Product

EXAMPLE 4

Deoxofluorination Conducted In-Situ without Isolation of Aminosulfur Trifluoride A solution of diphenylamine (25 mmol) in THF (25 mL) containing triethylamine (3.48 mL, 25 mmol) was added dropwise to a solution of $SF_4$ (37 mmol) in THF (75 mL) contained in a 3-neck flask equipped with a stirring bar, $N_2$ inlet tube, dry ice condenser, and $SF_4$ inlet tube (as described above) at $-78°$ C. The mixture was brought to $-10°$ C. and kept for 3 h. It was again cooled to $-78°$ C. and excess $SF_4$ was removed in-vacuo. The mixture was then treated with a THF (10 mL) solution of cyclooctanol (3.20 g, 25.0 mmol) and stirred at $-78°$ C. for 1 h. The reaction was quenched with 5 mL $H_2O$ and the solvents were evaporated in-vacuo, treated with satd. $NaHCO_3$ (200 mL), extracted into EtOAc, dried ($MgSO_4$), filtered, and evaporated in-vacuo to obtain the product as a mixture of cyclooctyl fluoride and cyclooctene (70:30 ratio).

EXAMPLE 5

A solution of diphenylaminosulfur trifluoride (25 mmol) in THF (100 mL) prepared as above was treated with a THF solution (10 mL) of 4-t-butylcyclohexanone (3.85 g, 25 mmol) at room temperature and stirred for 7 days. After work-up as described for the alcohol above, a product was obtained which was a mixture of 4-t-butyl-difluorocyclohexane and 4-t-butyl-1-fluorocyclohexene (96:4 ratio).

Additional examples of the fluorination method of the present invention with various target compounds to be fluorinated are set forth below.

EXAMPLE 6

Fluorination of phenethanol

A solution of phenethanol (122 mg, 1 mmol) in $CH_2Cl_2$ (5.0 mL) was added to diphenylaminosulfur trifluoride (308 mg, 1.2 mmol) at $-78°$ C.; under $N_2$; then brought to room temperature and stirred for 16 h. After work-up and purification as above phenethyl fluoride (75 mg, 60%) was obtained. $^1$H NMR in $CDCl_3$ d 7.7–7.4 (d, 2H), 7.3–7.1 (t, 2H), 7.1–7.0 (t, 1H). $^{19}$F ($CDCl_3$) d –215 (2F).

EXAMPLE 7

Fluorination of phenethanol

A solution of phenethanol (122 mg, 1 mmol) in $CH_2Cl_2$ (5.0 mL) was added to bismethoxyethyl aminosulfur trifluoride (265 mg, 1.2 mmol) at $-78°$ C.; under $N_2$; then brought to room temperature and stirred for 16 h. After work-up and purification as above phenethyl fluoride (85 mg, 68%) was obtained. $^1$H NMR in $CDCl_3$ d 7.7–7.4 (d, 2H), 7.3–7.1 (t, 2H), 7.1–7.0 (t, 1H). $^{19}$F ($CDCl_3$) d –215 (2F).

EXAMPLE 8

Fluorination of ethyl-2-hydroxybutyrate

A solution of ethyl-2-hydroxybutyrate (397 mg, 3 mmol) in $CH_2Cl_2$ (5.0 mL) was added to N-methyl-N-phenylaminosulfur trifluoride (877 mg, 4.5 mmol) at $-78°$ C.; under $N_2$ and stirred for 16 h. After work-up and purification as above ethyl-2-fluorobutyrate (362 mg, 90%) was obtained. $^1$H NMR in $CDCl_3$ d 4.3–4.1 (q, 2H), 1.55 (d, 6H), 1.3–1.1 (t, 3H). $^{19}$F ($CDCl_3$) d –148 (1F).

EXAMPLE 9

Fluorination of ethyl-2-hydroxybutyrate

A solution of ethyl-2-hydroxybutyrate (397 mg, 3 mmol) in $CH_2Cl_2$ (5.0 mL) was added to bis(methoxyethyl) aminosulfur trifluoride (994 mg, 4.5 mmol) at $-78°$ C.; under $N_2$ and stirred for 16 h. After work-up and purification as above ethyl-2-fluorobutyrate (362 mg, 90%) was obtained. $^1$H NMR in $CDCl_3$ d 4.3–4.1 (q, 2H), 1.55 (d, 6H), 1.3–1.1 (t, 3H). $^{19}$F ($CDCl_3$) d –148 (1F).

EXAMPLE 10

Fluorination of acetone cyanohydrin

A solution of acetone cyanohydrin (87 mg, 1 mmol) in $CH_2Cl_2$ (10.0 mL) was added to N-methyl-N-phenylaminosulfur trifluoride (292 mg, 1.5 mmol) at $-78°$ C.; under $N_2$; then brought to room temperature and stirred for 16 h. After work-up and purification as above 2-fluoro-2-methylpropionitrile (59 mg, 90%) was obtained. $^1$H NMR in ($CDCl_3$) d 1.75 (d, 6H). $^{19}$F ($CDCl_3$) d –138 (1 F).

EXAMPLE 11

Fluorination of 4-carboethoxycyclohexanone

A solution of 4-carboethoxycyclohexanone (170 mg, 1 mmol) in $CH_2Cl_2$ (5.0 mL) was added to N-methyl-N-phenylaminosulfur trifluoride (390 mg, 2.0 mmol) at $-78°$ C.; under $N_2$; then brought to room temperature and stirred for 16 h. After work-up and purification as above 1-carboethoxy-4,4-difluorocyclohexanone (134 mg, 70%) was obtained. $^1$H NMR in $CDCl_3$ d 5.3–5.1 (m, 1H), 4.34.0 (q, 2H), 2.7–1.6 (m, 8H), 1.25 (t, 3H). $^{19}$F ($CDCl_3$) d –94 (1F, dd) –100.5 (dd, 1F).

EXAMPLE 12

A solution of 4-carboethoxycyclohexanone (170 mg, 1 mmol) in $CH_2Cl_2$ (5.0 mL) was added to N-phenyl-N-4-chlorophenyl aminosulfur trifluoride (584 mg, 2.0 mmol) at $-78°$ C.; under $N_2$; then brought to room temperature and stirred for 16 h. After work-up and purification as above 1-carboethoxy-4,4-difluorocyclohexanone (134 mg, 70%) was obtained. $^1$H NMR in $CDCl_3$ d 5.3–5.1 (m, 1H), 4.3–4.0 (q, 2H), 2.7–1.6 (m, 8H), 1.25 (t, 3H). $^{19}$F ($CDCl_3$) d –94 (1F, dd) –100.5 (dd, 1F).

EXAMPLE 13

Fluorination of cyclooctanone

A solution of cyclooctanone (3.20 g, 25 mmol) in $CH_2Cl_2$ (5.0 mL) was added to diphenylaminosulfur trifluoride (6.43 g, 25 mmol) at -room temperature under $N_2$; and stirred for 7 days. After work-up as above difluorcyclooctanone was obtained in 30% yield (by g.c.) $^{19}$F ($CDCl_3$) d –99.5 (2F).

EXAMPLE 14

Fluorination of benzaldehyde

A solution of benzaldehyde (106 mg, 1 mmol) in $CH_2Cl_2$ (5.0 mL) was added to diphenyl aminosulfur trifluoride (386 mg, 1.0 mmol) at $-78°$ C.; under $N_2$; then brought to room temperature and stirred for 16 h. After work-up and purification as above benzal fluoride (128 mg, quantitative yield) was obtained. $^1$H NMR in $CDCl_3$ d 7.65 (d, 2H), 7.4 (t, 1H), 7.3 (t, 2H). $^{19}$F ($CDCl_3$) d –110 (2F).

EXAMPLE 15

A solution of benzaldehyde (106 mg, 1 mmol) in $CH_2Cl_2$ (5.0 mL) was added to bis(methoxyethyl) aminosulfur trifluoride (332 mg, 1.5 mmol) at $-78°$ C.; under $N_2$; then brought to room temperature and stirred for 16 h. After work-up and purification as above benzal fluoride (128 mg, quantitative yield) was obtained. $^1$H NMR in $CDCl_3$ d 7.65 (d, 2H), 7.4 (t, 1H), 7.3 (t, 2H). $^{19}$F ($CDCl_3$) d –110 (2F).

EXAMPLE 16

Fluorination of benzoic acid

A solution of benzoic acid (122 mg, 1 mmol) in $CH_2Cl_2$ (5.0 mL) was added to diphenylaminosulfur trifluoride (771 mg, 3.0 mmol ) under $N_2$ and stirred for 16 h at room temperature. After work-up as above benzoyl fluoride (124 mg, quantitative yield) was obtained. The product was identified by g.c.m.s. $M^+=124$

EXAMPLE 17

Fluorination of benzoyl chloride

A solution of benzoyl chloride (141 mg, 1 mmol) in $CH_2Cl_2$ (5.0 mL) was added to bis(methoxyethyl) aminosulfur trifluoride (567 mg, 3.0 mmol ) under $N_2$ and stirred for 16 h at room temperature. After work-up as above benzoyl fluoride (124 mg, quantitative yield) was obtained. The product was identified by g.c.m.s. $M^+=24$

EXAMPLE 18

Fluorination of phenyl methyl sulfoxide

A solution of methyl phenyl sulfoxide (140 mg, 1 mmol) in $CH_2Cl_2$ (5.0 mL) was added to bis(methoxyethyl) aminosulfur trifluoride (332 mg, 1.5 mmol ) under $N_2$ and stirred for 16 h at room temperature. After work-up as above fluoromethyl phenyl sulfide (70% yield as determined by NMR) was obtained. $^1$H NMR $(CDCl_3)$ d 7.5–7.0 (m, 5H), 3.3 (d, 2H). 19F NMR $(CDCl_3)$ d −183 (1 F).

EXAMPLE 19

Fluorination of cyclohexene oxide.

20 mmol of cyclohexene oxide and 24 mmol of Deoxofluor were charged to a 100 mL three neck, round bottom flask equipped with a stir bar, a condenser, a glass stopper, a gas inlet adapter and a septum. 4 mmol of ethanol was added to generate HF in-situ. The flask was heated to 60–70° C. for 30 h under N2. The reaction mixture was diluted in chloroform washed with saturated bicarbonate, dried Na2SO4), filtered and evaporated in vacuo. GC-MS indicated >95% conversion of the starting material to products. Two major products were observed in the $^{19}$F NMR. A multiplet was observed at −193 ppm and another multiplet at −182 ppm. These signals agree with literature values for 1,2 difluorocyclohexane and bis (fluorocyclohexyl) ether respectively. Integration of peaks indicate a product ratio of 1:2 difluoride/difluoroether

EXAMPLE 20

Fluorination of 4-t-butylcyclohexanone by diethylaminosulfur trifluoride(DAST) and N-ethyl-N-phenylaminosulfur trifluoride (a comparison).

(a) Fluorination with DAST

A solution of 4-t-butylcyclohexanone (308 mg, 2.0 mmol) in $CH_2Cl_2$ (10.0 mL) was added to diethylaminosulfur trifluoride (483 mg, 3.0 mmol ) at room temperature under $N_2$. $BF_3.OEt_2$ (100 mL) was added and the mixture was stirred for 6 h at room temperature. The mixture was washed with saturated $NaHCO_3$, dried $(Na_2SO_4)$, filtered and evaporated in vacuo. Proton and Fluorine NMR with 4-fluoroanisole (2 mmol) as internal standard showed that a 67% yield of 1,1-difluoro-4-t-butylcyclohexane was obtained.

(b) Fluorination with N-ethyl-N-phenylaminosulfur trifluoride

A solution of 4-t-butylcyclohexanone (308 mg, 2.0 mmol) in $CH_2Cl_2$ (10.0 mL) was added to N-ethyl-N-phenylaminosulfur trifluoride (627 mg, 3.0 mmol ) at room temperature under $N_2$. $BF_3.OEt_2$ (100 mL) was added and the mixture was stirred for 6 h at room temperature. The mixture was washed with saturated $NaHCO_3$, dried (Na2SO4), filtered and evaporated in vacuo. Proton and Fluorine NMR with 4-fluoroanisole (2 mmol) as internal standard showed that a 99% yield of 1,1-difluoro-4-t-butylcyclohexane was obtained.

EXAMPLE 21

Catalysis of fluorination by Lewis acids using N-methyl-N-phenylaminosulfurtrifluoride.

(a comparison)

(a) Fluorination of 4-t-butylcyclohexanone without Lewis acid catalyst

A reaction of 4-t-butylcyclohexanone (2 mmol) with N-methyl-N-phenylaminosulfur trifluoride (3.0 mmol) in $CH_2Cl_2$ (10 mL) at room temperature gave a 99% conversion to 1,1-difluoro-4-t-butylcyclohexane after 69 h. as determined by NMR (4-fluoroanisole as internal standard)

(b) With $BF_3.OEt_2$ as catalyst

A reaction of 4-t-butylcyclohexanone (2 mmol) with N-methyl-N-phenylaminosulfur trifluoride (3.0 mmol) in $CH_2Cl_2$ (10 mL) containing $BF_3.OEt_2$ (0.3 mmol) at room temperature gave a 99% conversion to 1,1-difluoro-4-t-butylcyclohexane after 6 h. as determined by NMR (4-fluoroanisole as internal standard)

(c) With $ZnI_2$ as catalyst

A reaction of 4-t-butylcyclohexanone (2 mmol) with N-methyl-N-phenylaminosulfur trifluoride (3.0 mmol) in $CH_2Cl_2$ (10 mL) containing $ZnI_2$ (0.3 mmol) at room temperature gave a 67% conversion to 1,1-difluoro-4-t-butylcyclohexane after 3 h. as determined by NMR (4-fluoroanisole as internal standard)

(d) With $TiCl_4$ as catalyst

A reaction of 4-t-butylcyclohexanone (2 mmol) with N-methyl-N-phenylaminosulfur trifluoride (3.0 mmol) in $CH_2Cl_2$ (10 mL) containing $TiCl_4$ (0.3 mmol) at room temperature gave a 67% conversion to 1,1-difluoro-4-t-butylcyclohexane after 3 h. as determined by NMR (4-fluoroanisole as internal standard).

EXAMPLE 22

Reaction of diethylaminosulfur trifluoride with 4-t-butylcyclohexanone (with and without Lewis acids)

(a) Without Lewis acid

A reaction of 4-t-butylcyclohexanone (2 mmol) with diethylaminosulfur trifluoride (3.0 mmol) in $CH_2Cl_2$ (10 mL) at room temperature gave a 99% conversion of starting material to products and a 67% yield of 1,1-difluoro-4-t-butylcyclohexane after 6 h.as determined by NMR (4-fluoroanisole as internal standard).

(b) With BF₃.OEt₂ as catalyst

A reaction of 4-t-butylcyclohexanone (2 mmol) with diethylaminosulfur trifluoride (3.0 mmol) in CH₂Cl₂ (10 mL) containing BF3.OEt2 (0.3 mmol) at room temperature gave a 99% conversion of starting material to products and a 67% yield of 1,1-difluoro-4-t-butylcyclohexane after 6 h.as determined by NMR (4-fluoroanisole as internal standard).

(c) With ZnI₂ as catalyst

A reaction of 4-t-butylcyclohexanone (2 mmol) with diethylaminosulfur trifluoride (3.0 mmol) in CH₂Cl₂ (10 mL) containing ZnI2 (0.3 mmol) at room temperature gave a 99% conversion of starting material to products and a 67% yield of 1,1-difluoro-4-t-butylcyclohexane after 6 h.as determined by NMR (4-fluoroanisole as internal standard).

(d) With TiCl₄ as catalyst

A reaction of 44-butylcyclohexanone (2 mmol) with diethylaminosulfur trifluoride (3.0 mmol) in CH₂Cl₂ (10 mL) containing TiCl₄ (0.3 mmol) at room temperature gave a 99 % conversion of starting material to products and a 67% yield of 1,1-difluoro-4-t-butylcyclohexane after 6 h.as determined by NMR (4-fluoroanisole as internal standard).

The present invention provides a high yielding, preferably one-step, process for the preparation of a number of classes of novel aminosulfur trifluoride compounds. These novel aminosulfur trifluoride compounds have been shown to have unique performance for effecting deoxofluorination of alcohols and ketones as demonstrated by the presently reported thermal analysis studies indicating that they are safer to use than the currently available dialkylaminosulfur trifluorides (DAST), see the data in Table 7 for gas pressure generated per millimole of reagent decomposed, and more effective at fluorinating alcohols than (S)-2-(methoxyethyl) pyrrolidin-1-yl sulfur trifluoride, see Table for the efficiency of fluorination showing poor fluorination by the latter compound in contrast to the compounds of the present invention.

The simplicity of the method used for preparing the new aminosulfur trifluorides combined with their safety and simplicity in use should make these compounds attractive for large scale commercial production and use, providing unexpected improvement in fluorination technology in contrast to the industry avoidance of DAST for such fluorinations.

The present invention has been set forth with regard to several preferred embodiments, but the full scope of the present invention should be ascertained from the claims which follow.

We claim:
1. A method for the fluorination of a compound selected from the group consisting of alcohols, aldehydes, ketones, epoxides and mixtures thereof using a fluorinating reagent comprising contacting said compound with said fluorinating reagent under conditions sufficient to fluorinate said compound wherein said fluorinating reagent is an aminosulfur trifluoride composition having a structure with one or more:

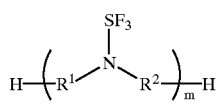

wherein m=1–5 and $R^1$ and $R^2$ are:

(1) when m=1, one of $R^1$ and $R^2$ is an aryl radical and the other is an at least 5 member saturated cyclic hydrocarbon radical having one to three heteroatoms selected from the group consisting of oxygen; or (2) when m=1, one of $R^1$ and $R^2$ is an aryl radical and the other is an at least 5 member saturated cyclic hydrocarbon radical having one to three heteroatoms selected from the group consisting of oxygen wherein said cyclic hydrocarbon radical is fused to said aryl radical; or (3) when m=1, $R^1$ and $R^2$ an together a cyclic ring having 2 to 10 carbon ring members and 1 heteroatom selected from the group consisting of oxygen, nitrogen and alkylated nitrogen wherein said ring has 1 to 2 alkoxyalkyl functionalities; or (4) when m=1, $R^1$ and $R^2$ an together an unsaturated cyclic ring having 2 to 4 carbon ring members and one to three heteroatoms selected from the group consisting of oxygen, nitrogen, protonated nitrogen and alkylated nitrogen wherein said ring has one to three functional groups of alkoxy; or (5) when m=1, individually alkoxyalkyl radicals; or (6) when m=1, one of $R^1$ and $R^2$ is alkoxyalkyl and the other is selected from the group consisting of alkyl and aryl radicals; or.

2. The method of claim 1 wherein said compound is selected from the group consisting of alcohols, and mixtures thereof.

3. The method of claim 1 wherein said composition has the structure:

wherein $R^{1-3,\ 6-8}$ are individually H, normal or branched alkyl $C_{1-10}$ or aryl $C_{6-10}$ and $R^{4-5}$ are $C_{2-10}$ normal or branched alkyl.

4. The method of claim 3 wherein said composition has the structure:

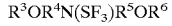

wherein $R^3$ and $R^6$ are individually $C_1$ to $C_{10}$ in a normal or branched chain alkyl and $R^4$ and $R^5$ are $C_{2-10}$ normal or branched alkyl.

5. The method of claim 3 wherein said composition has the structure:

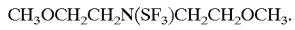

6. The method of claim 1 wherein said fluorination is conducted in the presence of a solvent.

7. The method of claim 6 wherein said solvent is selected from the group consisting of paraffins, halocarbons, ethers, nitriles, nitro compounds and mixtures thereof.

8. The method of claim 1 wherein the fluorination is conducted under anhydrous conditions.

9. The method of claim 6 wherein said fluorination is conducted at a temperature above the freezing point of said solvent and below the boiling point of said solvent.

10. The method of claim 1 wherein said compound is a ketone and the fluorination is catalyzed with at least a catalytic amount of a Lewis acid.

11. The method of claim 10 wherein said Lewis acid is selected from the group consisting of $BF_3$, $ZnI_2$, $TiCl_4$ and mixtures thereof.

12. The method of claim 1 wherein said compound is a ketone and at least a catalytic amount of HF is added to said fluorination.

13. The method of claim 2 wherein said alcohol is selected from the group consisting of monofunctional and polyfunctional primary, secondary, tertiary and vinyl alcohols and mixtures thereof.

14. The method of claim 1 wherein said aldehyde is selected from the group consisting of aliphatic, aromatic and heterocyclic aldehydes and mixtures thereof.

15. The method of claim 1 wherein said ketone is selected from the group consisting of aliphatic, aromatic and heterocyclic ketones and mixtures thereof.

16. The method of claim 1 comprising synthesizing said aminosulfur trifluoride composition from a secondary amine and $SF_4$ in a reaction media and without isolating said aminosulfur trifluoride composition, fluorinating said compound with said aminosulfur trifluoride composition by contact of said compound with said aminosulfur trifluoride in said reaction media.

17. The method of claim 16 wherein a tertiary amine is present during the synthesizing of said aminosulfur trifluoride.

18. The method of claim 17 wherein a solvent is present during the synthesizing of said aminosulfur trifluoride.

19. The method of claim 16 wherein said aminosulfur trifluoride is a dialkyl aminosulfur trifluoride.

20. The method of claim 19 wherein said dialkyl aminosulfur trifluoride is diethylaminosulfur trifluoride.

* * * * *